United States Patent [19]

Mileaf et al.

[11] Patent Number: 5,679,584
[45] Date of Patent: Oct. 21, 1997

[54] METHOD FOR CHEMICAL DETECTION

[76] Inventors: Daryl Sunny Mileaf, 6411 Hanover Crossing Way, Hanover, Md. 21076; Noe Esau Rodriquez, II, 312 Hollyberry Rd., Severna Park, Md. 21146

[21] Appl. No.: 434,421

[22] Filed: May 3, 1995

[51] Int. Cl.$^6$ .................. G01N 33/546; G01N 21/00; G01N 21/03; G01N 21/75
[52] U.S. Cl. .................. 436/533; 422/58; 422/61; 422/68.1; 436/164; 436/165; 436/514; 436/518; 436/519; 436/520; 436/524; 436/527; 436/528; 436/529; 436/534; 436/805; 436/808; 436/809
[58] Field of Search .................. 422/58, 61, 68.1; 436/164, 165, 514, 518, 519, 520, 524, 527, 528, 529, 534, 805, 808, 809, 533

[56] References Cited

U.S. PATENT DOCUMENTS

| | | | |
|---|---|---|---|
| 4,963,498 | 10/1990 | Hillman et al. | 436/69 |
| 5,209,904 | 5/1993 | Forney et al. | 422/73 |
| 5,290,517 | 3/1994 | Samuels et al. | 422/58 |
| 5,491,095 | 2/1996 | Bepko et al. | 436/518 |
| 5,500,187 | 3/1996 | Deoms et al. | 422/58 |
| 5,567,627 | 10/1996 | Lehnen | 436/518 |

OTHER PUBLICATIONS

"The Illicit Substance Detector" by Daryl S. Mileaf, Joseph Leginus, Ph.D. and Noe E. Rodriguez, II, Westinghouse Electric Corporation, Baltimore, MD to be published in Proceedings From Government Microcircuit Applications Conference 1994.

*Primary Examiner*—Toni R. Scheiner
*Assistant Examiner*—Sheela J. Huff

[57] ABSTRACT

A method for detecting a target substance which includes collecting a substance sample; introducing the substance sample into a substance card having at least one reagent responsive to the presence of the target substance and having a light-transmissive chamber; inserting the substance card into a substance detector device having a photosensor and adapted to receive the substance card; mixing the substance sample with the reagents for a preselected mixing period, thus producing a measurand having a target substance reaction; streaming the measurand through the light-transmissive chamber and illuminating the measurand with a quantity of light for a selectable analysis period, an optical characteristic of the measurand can be measured with the photosensor; and selecting the target substance reaction as a positive reaction or a negative reaction, responsive to the optical characteristic. If the target substance reaction is a negative reaction, the device operator is signalled thereof. On the other hand, if the target substance reaction is the positive reaction, the streaming, illuminating, measuring, and selecting steps are repeated for a selectable number of repetitions. If the target substance reaction remains positive after exhausting the selectable number of repetitions, the device operator is signalled of the positive reaction.

10 Claims, 4 Drawing Sheets

METHOD FOR CHEMICAL DETECTION

BACKGROUND OF THE INVENTION

1. Field of the Invention

The invention herein pertains to a method for chemical detection, in particular, to a method for chemical detection using a latex agglutination reaction using an illicit substance detector.

2. Description of the Prior Art

Recently, illicit substance detectors (ISD) have been developed to detect minute traces of target substances at the site where the sample is obtained. The ISD is a portable electronic device which can use the latex agglutination reaction to detect target substances of interest in microgram quantities. One such ISD is described in U.S. patent application Ser. No. 08/067,278, filed May 26, 1993, entitled "Method and System for Detecting Chemical Substances" now U.S. Pat. No. 5,491,095 which is incorporated herein by reference. ISDs are generally intended to provide rapid, on-site detection of substances of interest and may be used by law enforcement officers such as United States custom agents to screen samples in the field, for example, points of entry into the United States, to determine whether certain illicit substances are present.

With current ISDs, each analysis requires the use of a disposable substance card which contains the reagents needed to perform the analysis reaction, and a viewing chamber by which the product of the reaction can be optically analyzed. Such a disposable substance card is described, for example, in U. S. patent application Ser. No. 986,816, filed Dec. 8, 1992, entitled "Disposable Optical Agglutination Assay and Method for Use" now U.S. Pat. No. 5,500,187, which is incorporated by reference. After a sample is obtained, it is introduced into the substance card, and the card is introduced into the ISD. The ISD manipulates the substance card to effect the mixing of test reagents with the substance sample, the product of the mixing can be called a measurand. Typically, the analysis can modify an optical characteristic of the measurand and thus requires the illumination of the viewing chamber containing the measurand so that the optical characteristic can be observed. The resultant optical characteristic in the measurand is then analyzed over a single, preset time period and determined to be "positive" or "negative" for the particular test at hand.

It may be desirable to test for multiple illicit substances at a particular testing location, e.g., a border checkpoint or an airport. However, ISDs such as the aforementioned device in Ser. No. 08/067,278 were designed, and are intended to be used for, a single type of illicit substance detection. For example, an ISD that is designed for detecting cocaine cannot detect whether a substance card specific to another target substance such as gun powder residue, has been inserted. Without that information, the ISD may not perform the analysis for an appropriate period of time, unless that time happens to coincide with the particular amount of time required by the cocaine-reagent reaction.

One approach to permitting an ISD to detect more than one type of target substance is to modify the substance cards so that each card-type had a recognizable, unique feature. With the current ISD design, the unique-card approach would require the ISD to itself be physically modified to add a recognition component for each unique card feature, so that the ISD can select the appropriate analysis for the type of material being analyzed. Modifications of substance cards and ISDs are undesirable because of the attendant added complexity, expense and deployment difficulties. What is needed is a method for detecting a target substance which permits an existing ISD to perform multiple analysis for a variety of illicit substances without requiring the modification of the ISD hardware or the provision of a unique feature to each of the disposable target substance cards.

SUMMARY OF THE INVENTION

The invention herein provides a method for detecting a target substance which includes collecting a substance sample; introducing the substance sample into a substance card having at least one preselected reagent responsive to the presence of the target substance and having a light-transmissive chamber; and inserting the substance card into a substance detector device having a photosensor and adapted to receive the substance card. Once the substance detector card has been inserted into the substance detector, the method continues by mixing the substance sample with the preselected reagents for a preselected mixing period, thus producing a measurand having a target substance reaction. After mixing, the method can include measuring an empty value by illuminating the light-transmissive chamber with a predetermined amount of light, and detecting with the photosensor a portion of the predetermined amount of light corresponding to the light-transmissive chamber being generally empty.

By streaming the measurand through the light-transmissive chamber and illuminating the measurand with a predetermined quantity of light for a selectable analysis period, an optical characteristic of the measurand can be measured with the photosensor. In general, the optical characteristic corresponds to the particular target substance reaction. Responsive to the optical characteristic, the method selects the reaction to be a positive reaction or a negative reaction. The positive reaction indicates the presence of the target substance in an amount greater than a first preselected sensitivity amount. On the other hand, the negative reaction indicates the presence of the target substance in an amount generally less than the preselected sensitivity amount.

The method can use a latex agglutination reaction to produce the target substance reaction. Because the latex agglutination assay can be produced for a wide range of substances, the classes of target substances which can be tested include drugs, explosives, and residues thereof.

If the target substance reaction is a negative reaction the device operator is apprised thereof by signalling the negative reaction on the device. However, if the target substance reaction is a positive reaction, the analysis continues by repeating the aforementioned streaming and illuminating of the measurand, measuring the optical characteristic of the measurand and selecting the type of reaction for a selectable number of repetitions. Each repetition can have a selectable analysis period corresponding to a respective repetition. If the reaction type has remained as a positive reaction for each of the selectable number of repetitions, then the target substance is considered positive, and the device is signaled thereof.

The optical characteristic measured in the measurand can be light transmissivity, or light intensity variation, or both. In a positive reaction, the light transmissivity generally is greater than a first predetermined transmissivity threshold and the light intensity variation generally is less than a first predetermined intensity variation threshold. On the other hand, the negative reaction, the light transmissivity generally is less than a second predetermined transmissivity threshold, and the intensity variation generally is greater than a second predetermined intensity variation threshold. In general, the first transmissivity threshold generally is greater than the second transmissivity threshold and the second intensity variation threshold generally is greater than the first intensity variation threshold.

The target substance reaction can be monitored for an invalidating condition, an invalid reaction can be selected upon the occurrence of said invalidating condition, and the invalid reaction can be signalled to the device operator. The invalidating conditions can include missing substance card, defective substance card, misaligned substance card, impaired substance detector device, large bubble formation within the light-transmissive chamber, and streaking of the target substance reaction in the light-transmissive chamber.

In one embodiment of the invention herein the selectable number of repetitions is three which includes first, second, and third selectable analysis periods, with the first selectable analysis period following the preselected mixing period. In addition, in one embodiment of the present invention, the preselected mixing period is about ten seconds, the first selectable analysis period is about ten seconds, the second selectable analysis period is about fifteen seconds, and the third selectable analysis period is about ten seconds.

Other details, objects, and advantages of the invention will become apparent as the following description of certain present preferred embodiments thereof proceeds. The accompanying drawings show presently preferred embodiments of the invention.

DETAILED DESCRIPTION OF THE PREFERRED EMBODIMENTS

The method according to the invention herein permits the use of existing ISD hardware and target substance product cards without requiring expensive physical modification of either ISD or card, avoiding the need for either making an ISD for each type of target substance to be detected or modifying existing ISD readers to detect an encoded physical feature that would be specific to the type of target substance detected, and creating a unique, ISD-readable feature for each substance card type.

Examples of classes of target substances which can be detectable using the method described herein include explosives, drugs having a high potential for abuse, such as pharmaceutical depressants and stimulants, psychoactive substances, and residues thereof. A pharmaceutical depressant as used herein can include substances, natural, semisynthetic, or synthetic, that depress the activity of the central nervous system, including opioids, barbiturates, and the like. Opioids and related substances can include, for example, opium, heroin, morphine, codeine, methadone, naloxone, and the like. A pharmaceutical stimulant as used herein can include central nervous system stimulants, such as, for example, cocaine and amphetamines, notably methamphetamine, and their derivatives. Psychoactive substances can include marijuana, lysergic acid diethylamide (LSD), and the like. Another type of target substance is gun powder residue and explosives including, for example, nitroglycerin, nitrocellulose, and so on.

The operation of an ISD is based upon a chemical reaction which can change an optical characteristic of a measurand. Although other chemical reactions causing an alteration in an optical characteristic of a measurand can be employed, the latex agglutination assay is the precipitation reaction currently preferred to be used with the ISD. The latex agglutination assay is a passive agglutination reaction in which a target substance antigen is adsorbed onto latex particles. The latex particles clump together in the presence of the antibody specific for the adsorbed antigen. Antibodies are proteins which are produced in warm-blooded animals in response to the presence of foreign material including viruses, drugs, and bacteria.

In such reactions, a substance sample is introduced to a mixture of reagents containing the latex particles and antibodies that are specific to the target substance of interest. Antibodies are attractive sensing elements because of two features: they are able to recognize very small quantities of material and they respond with a high degree of specificity, producing a low false-positive rate. If the target substance is not present, or is present in a quantity less than a sensitivity threshold quantity, the agglutination reaction is generally unimpeded and the latex molecules will aggregate, thus forming visible clumps in the measurand. On the other hand, where the target substance is present in quantities greater than the sensitivity threshold amount, agglutination will be inhibited and the measurand remains milky. Given the nature of these reactions, an ISD can use an optical characteristic such as light transmissivity or light intensity variation, or both, to determine if a reaction is negative or positive.

All latex agglutination assays for which target substance antibodies have been developed share the common feature of indicating a negative reaction by the formation of visible latex clumps. However, latex agglutination assays for different target substances can have different rates of agglutination and therefore, require different analysis periods to account for varied rates of reaction.

In general, the rate of agglutination, and the conditions under which the latex agglutination reaction will behave in a desired manner, vary with the nature and quantity of target substance of interest, the reagents used to detect the target substance, and the ambient temperature under which the test is performed. For a particular substance-reagent mixture, the agglutination reaction can be accelerated by higher temperatures and inhibited by lower temperatures. Low ambient temperatures, for example 45° F. and below, can inhibit the agglutination reaction to the extent that a false positive may result.

The method according to the invention herein can provide analyses for multiple illicit substances in devices such as current ISDs and can help offset less-than-desirable environmental testing conditions by providing for a selectable number of repetitions of analysis periods with the lengths of the analysis periods themselves being selectable to suit the suite of target substance analyses that the ISD can be expected to perform.

One need of ISD device users is that the agglutination reaction be recognized as quickly as possible to reduce the amount of time necessary to perform a given analysis. A rapid negative feature is useful in situations such as at a busy United States entry port where customs agents must screen a large number of persons and their belongings for trafficking in illicit substances. Given that most results are likely to be negative, the overall inconvenience to the public can be minimized by quickly providing a negative determination so that an individual may continue on their way past the entry point. The method according to the invention herein can conclude testing as soon as a negative target substance reaction is recognized, and inform the user of the results by signalling the negative result on the ISD.

One embodiment of the method for detecting a target substance according to the invention herein can include using a substance detector device such as the ISD described in U.S. patent application Ser. No. 08/067,278. A disposable sampling swab can be provided which contains small raised nubs for collecting the substance sample by rubbing against a surface potentially contaminated with the target substance. The method also includes introducing the substance sample into the substance card having the preselected reagents, and inserting the substance card into the substance detector device, which energizes the substance detector device.

The initialization of the detector device includes measuring the empty value of the light-transmissive viewing chamber. The empty value in general light transmissivity may be regarded as the light transmissivity while the chamber is generally empty.

After the initialization, the stepper motor of the device operates at high speed, mixing the substance sample and preselected reagents together and urging the mixture into the light-transmissive viewing chamber. When the substance sample and reagents have reached the chamber, the method continues by mixing the substance sample with the reagents until the expiration of a preselected mixing period, using the stepper motor at low speed. During this period, the light source can be turned off. This mixing produces a measurand having a target substance reaction that can be subject to a selectable number of analysis repetitions. In the present embodiment, two such repetitions are preferred, for a total of three analyses. In general, the measurand initially is milky white and translucent. The mixing period can be short, for example, 10 seconds, depending upon the reagents used in the particular substance assay and the aggressiveness of the antibodies used in the reaction.

After the mixing, each analysis proceeds by streaming the measurand through the light-transmissive viewing chamber, illuminating the measurand with a predetermined quantity of light during a selectable analysis period, and measuring an optical characteristic of the measurand with the photosensor. The photosensor can include a plurality of photodetector elements, or channels. The channels may be arranged to provide suitable analysis of the light transmitted from the light source. For example, the channels may be disposed perpendicularly to the measurand or, as in one preferred embodiment, the channels may be disposed transversely to the measurand flow. The optical characteristic is representative of the nature of the target substance reaction. During each selectable analysis period, the optical characteristic of the measurand is measured at specified intervals, for example 250 milliseconds.

The method further includes selecting the target substance reaction as a positive reaction or a negative reaction, responsive to the optical characteristic of the measurand as detected by the detector device photosensor. A positive reaction is one in which the presence of the target substance is detected in an amount generally greater than a sensitivity threshold amount. A negative reaction indicates the presence of the target substance in an amount generally less than the sensitivity threshold amount.

If, during one of the selectable analysis periods, the target substance reaction is a negative reaction, the device can signal the operator thereof, and testing can then be terminated. On the other hand, if the target substance reaction indicates a positive reaction, the device will reanalyze the target substance reaction for a selectable number of repetitions, with each selectable analysis period being tailored to the respective repetition. In one embodiment the total analysis period can be approximately 45 seconds of operation. At present, three analysis periods can be used during the total analysis period to accommodate the different reaction rates of different reagent sets. For example, heroin reagents typically show negative reactions within 12 to 15 seconds, while cocaine reagents typically show negative reactions within 30 to 33 seconds, and other reactions may take 37 to 45 seconds to form a negative reaction.

Where the target substance reaction is initially determined to be a positive reaction, the analysis method continues by streaming the measurand through the light-transmissive chamber, illuminating the measurand with a predetermined quantity of light for the selectable analysis period corresponding to that respective repetition, and measuring the optical characteristic of the measurand corresponding to the target substance reaction. To reduce the incidence of anomalous results, an analysis parameters can be reset between the selectable analysis periods. If during a selectable analysis period, the target substance reaction is determined to be negative, such negative reaction can be indicated to the operator by the detector device signaling the negative reaction, and halting additional analysis. If, on the other hand, the target substance reaction continues to be a positive reaction after the selectable number of repetitions of analyses have been exhausted, the operator is notified of the positive reaction by the signaling thereof.

The optical characteristic which can be used to determine the type of target substance reaction can include light transmissivity or the light intensity variation, or both. As used herein, light transmissivity is the degree to which light may be transmitted through the measurand as measured by comparing the portion of light transmitted through the measurand in the viewing chamber to the portion of light transmitted through an empty viewing chamber. Because, in a negative reaction, the measurand is generally a clear fluid populated with agglutinated latex clumps, the light transmissivity will be generally high and above a first preselected transmission threshold. In addition, because of the latex clumps in the measurand, individual elements of the photosensor can be temporarily occluded by the passing latex clumps, thus causing a light intensity variation to be greater than the first predetermined light intensity variation threshold.

On the other hand, a target substance reaction that is a positive reaction will tend to remain milky and translucent. The light transmissivity of the measurand to the photosensor is generally below a second transmission threshold, which is in turn generally less than the first transmission threshold. Because of the minute size of the unagglutinated latex particles, light intensity variation is generally less than a first predetermined light intensity variation threshold and tends to be small in comparison to the light intensity variation in the negative sample scenario.

In addition to a positive reaction and negative reaction, the target substance reaction can also be an invalid reaction.

Invalidating conditions which can lead to an invalid reaction include a missing substance card, a defective substance card, a misaligned substance card, and an impaired substance detector device. A defective substance card can result from a card having insufficient reagent, a damaged viewing chamber, and so on. Similarly, an impaired substance detector device can be the result of a damaged photosensor, a failing battery, and the like. Invalidating conditions can also include large bubble formation within the light-transmissive viewing chamber and streaking of the target substance reaction within the light-transmissive viewing chamber.

An invalid reaction due to large bubble formation can be indicated by the light transmissivity exceeding a second predetermined light transmissivity threshold, or the light intensity variation being less than the first predetermined light intensity variation threshold, or both. The second predetermined transmissivity threshold can also be referred to as the bubble threshold, which can be a preselected percentage of the empty chamber valve. For example, the bubble value can be 70 percent of the empty chamber value so that if the light transmissivity of the measurand is equal to, or greater than, 70 percent of the empty chamber value, a bubble is recognized.

An invalid reaction due to streaking can be indicated by the light transmissivity being generally less than the first predetermined transmission threshold, or the light intensity variation being greater than a second intensity variation threshold, or both. Because some streaking can exist during testing without deleterious effects on test accuracy, the second intensity variation threshold can be set as a low pass filter value (LPFV) so that streaking variations below the LPFV can be ignored. In general, the second transmission threshold is generally greater than a first transmission threshold and the second intensity variation threshold is generally greater than the first intensity variation threshold.

In the embodiment herein with two selectable repetitions, providing three selectable analysis periods, a negative reaction can stop an analysis within any period. However, during a full (positive) run, the first analysis period can last for about 12 to 15 seconds for fast acting reagents, such as heroin antibodies, the second analysis period can last about 25 to 35 seconds for moderately reacting reagents, such as cocaine reagents, and the third analysis period can last about 37 to 45 seconds for slower reactions, lower temperatures, and threshold amounts of target substance in the substance sample. If the target substance reaction of the measurand has remained positive during all three analysis periods, the analysis is concluded at the end of the 45-second, three-analysis-period multiple-substance analysis, the stepper motor is retracted, and the operator is signaled of the positive result by the detector device.

The multiple selectable repetition, selectable analysis period substance detection method according to the invention may be better understood by reference to the process flow diagram in FIGS. 1a through 1d. The ISD device operation and substance analysis begins when the operator inserts a substance card into the ISD. As indicated in step 10, the substance detector device is initialized and several self-tests are performed on the detector device and the card. For example, in step 10 the self-tests can include a missing, defective, or misaligned substance card, or an impaired substance detector device. If the detector device does not pass any of the self-tests, further operation of the device is terminated and the FAIL status of the self-test is signaled to the operator on the device display. Assuming the outcome of the self-test at step 20 was PASS, the device commences operating with the stepper motor at high speed. During the initialization process, the CPU of the detector device is initialized, the light source is turned on, the initial values of the photodetector channels are obtained, thereby producing the aforementioned empty chamber value, and a speed change threshold value.

Figure 1A:
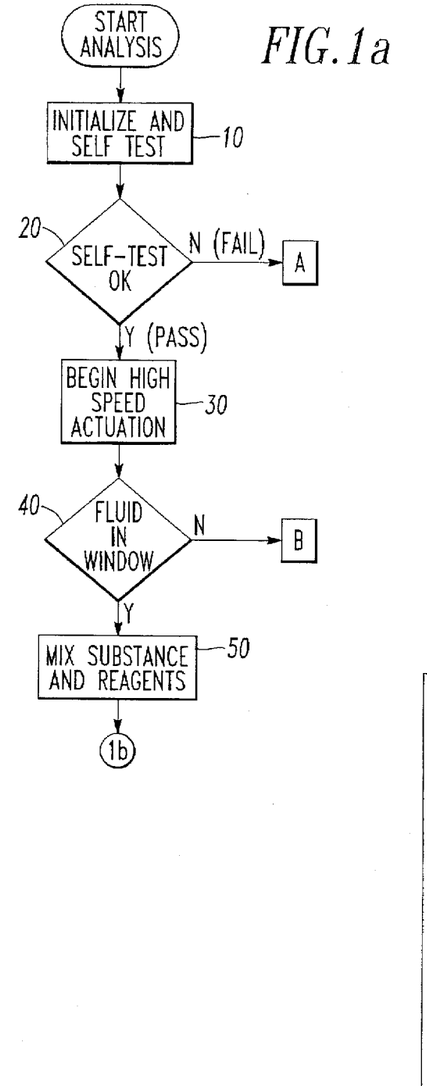
FIGS. 1a–1d are flow diagrams of one embodiment of the method according to the invention herein.

During high speed operation, the light-transmissive viewing chamber, or window, is monitored for the presence of the fluid containing the sample substance and reagent mixture, as seen in step 40. If, after a preset period, no fluid is detected in the viewing chamber, testing is aborted and the operator is signaled of the abort status. As indicated in FIG. 1a, when fluid is detected in the viewing chamber, high speed operations are begun so that the sample substance and the reagents may be sufficiently mixed to produce a measurand, as indicated in step 50. The mixing at step 50 proceeds for a preselected mixing period and can include movement of the fluid alternately in a forward direction and a reverse direction. During the mixing period at step 50, the light source may be turned off in order to reduce power consumption by the device. After the predetermined mixing period at step 50 has been completed, parameters such as counters, filter values and threshold values can be reset, and the light source turned on as indicated at step 60 in FIG. 1b. One key parameter that may be selected at step 60 is the length of time desired for the imminent selectable analysis period. Low speed operation of the device stepper motor may continue, streaming the measurand through the viewing chamber. As the measurand passing through the viewing chamber, an optical characteristic of the measurand is determined for each channel of the plurality of photodetectors in the photosensor.

Figure 1B:
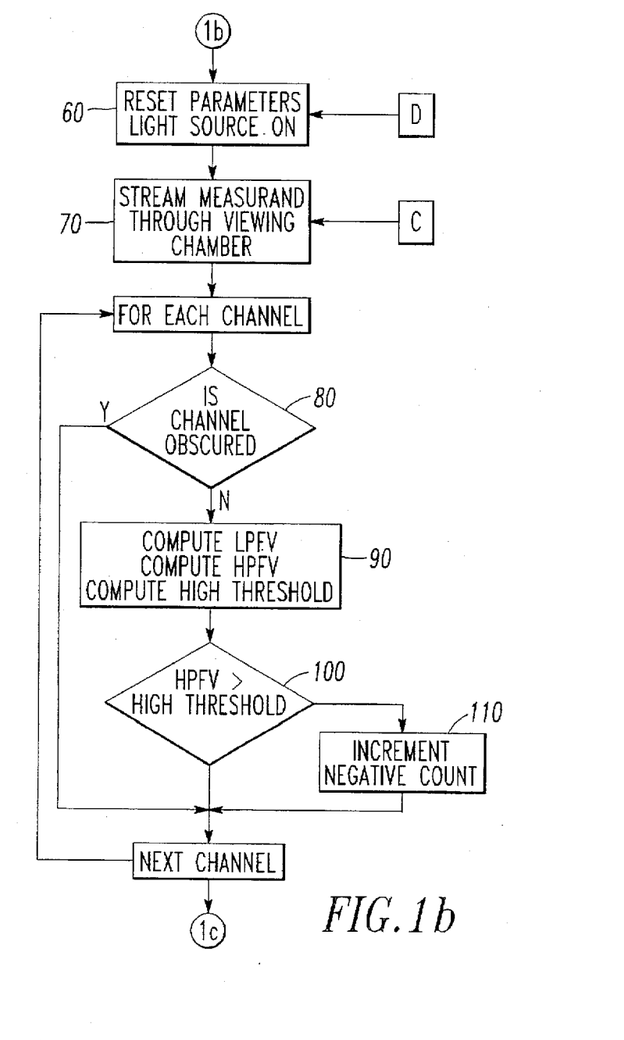
Figure 1C:
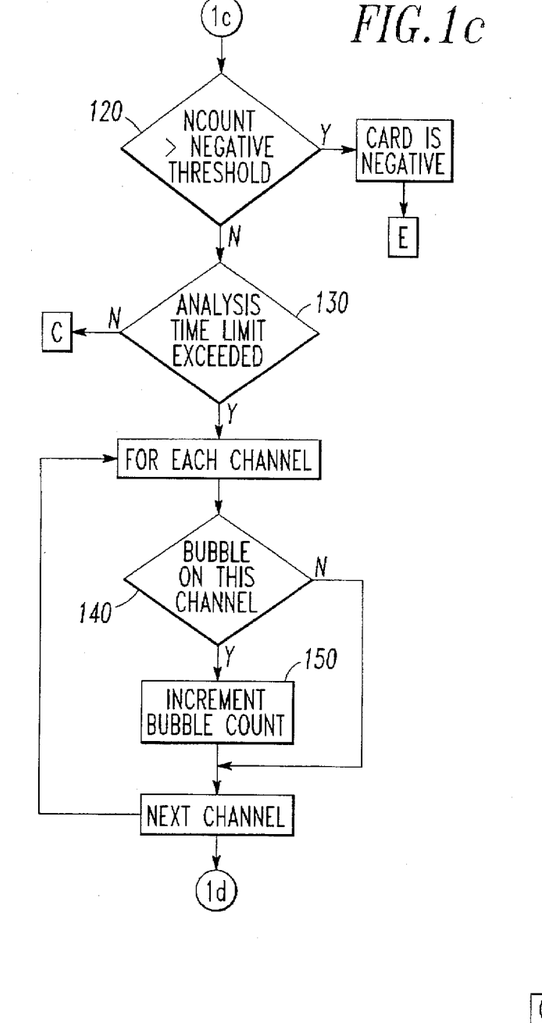
Figure 1D:
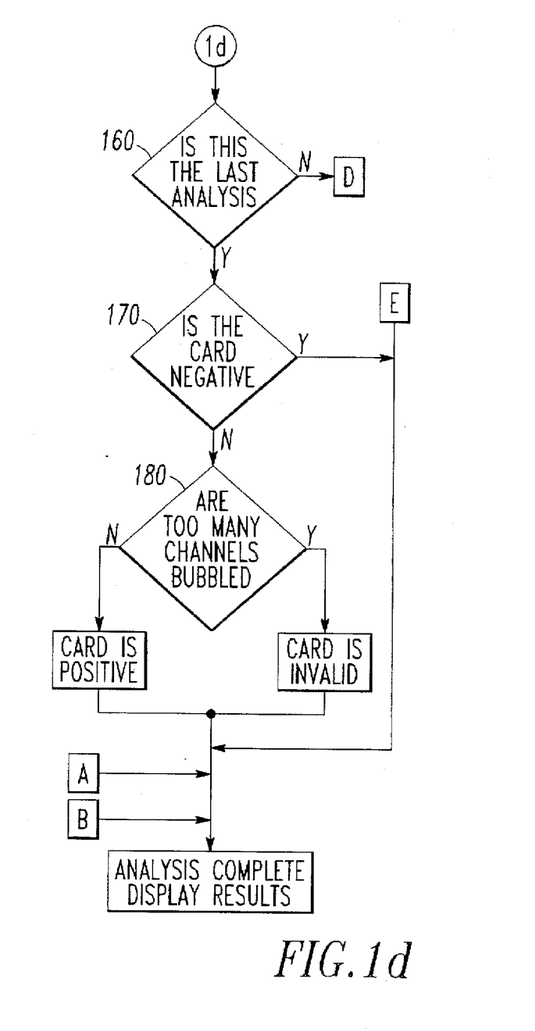

As at step 80, each channel is checked for obscuration. Such obscuration can be determined by comparing the light transmitted to each channel through the substance detector card. If the amount of light detected for a particular channel is less than a preset constant threshold value, the channel is considered obscured and testing of the next channel for obscuration proceeds. As indicated at steps 80 and 90, if the channel is determined to be not obscured, an optical characteristic of the measurand is analyzed, and light intensity variation values are computed. Where a plurality of channels are used, it may be desirable to provide the desired test and threshold values using high pass and low pass filtering in order to facilitate the selection of a high pass filter value (HPFV) and a low pass filter value (LPFV), respectively. Also, a high pass threshold value is calculated. If the HPFV is greater than the high pass threshold for a particular channel, the measurand is considered to be negative at that channel, and subsequent channels are likewise processed through steps 80, 90, 100 and 110 seriatim until all channels have been analyzed. For each HPFV greater than the high pass threshold determined at step 100, a negative count is incremented as at step 110. The cumulative value of the negative count, or NCOUNT, is compared at step 120 to a preselected negative threshold. If the negative count is greater than the aforementioned negative threshold, the target substance reaction is deemed to be negative, and the operator is signaled of the negative status thereof. Steps 70–120 are repeated, as indicated at step 130, until a selectable analysis period has been completed. The selectable analysis period can be associated with a respective repetition. Note that during the execution of steps 80–110 the accumulation of a negative count at step 110 which is in excess of the predetermined negative threshold will, at step 120, direct the analysis to completion with a NEGATIVE status. In this way, rapid termination of testing can be obtained as soon as a negative target substance reaction has sufficiently developed.

After the respective selectable analysis period has completed at step 130, each channel is analyzed for the presence of a bubble at step 140. A bubble can be detected on a particular channel by the presence of a high light transmissivity and a low light intensity variation. Where a bubble is detected on a particular channel at step 140, the aggregate bubble count is incremented at step 150.

As stated above, the overall analysis can include a selectable number of repetitions so that multiple, i.e., two or more, target substance reaction analyses can be provided. If the last of the preselected number of repetitions has not been completed, the analysis is resumed at step 60 wherein parameters such as LPFV, HPFV, high pass threshold and other counters are reset, and the next selectable analysis period proceeds. After the last repetition of the selectable analysis period has been sensed at step 160, the light transmissivity and light intensity variation are again measured to determine whether the target substance reaction is a negative reaction. If it is determined to be a negative reaction, the negative status is signaled to the operator on the device display. If, on the other hand, the card is deemed not to be negative, the value in the bubble count counter, which is incremented at step 150, is evaluated at step 180. Because small bubbles, as indicated by a "few" number of channels be "bubbled", do not substantially impair the analysis, only bubbles which occupy at least a preselected number of channels will be considered to create a target substance reaction of INVALID at step 180. However, if the size or number of bubbles is sufficiently small, as determined at step 180, and the reaction has not been determined to be a negative reaction at step 170, the target substance reaction is deemed to be positive. The positive status is signaled to the operator on the device display. It can be seen from FIGS. 1a through 1d that a target substance reaction may not be deemed POSITIVE unless each of the repetitions of target substance analysis has remained positive to each of the selectable analysis periods.

Figure 2:
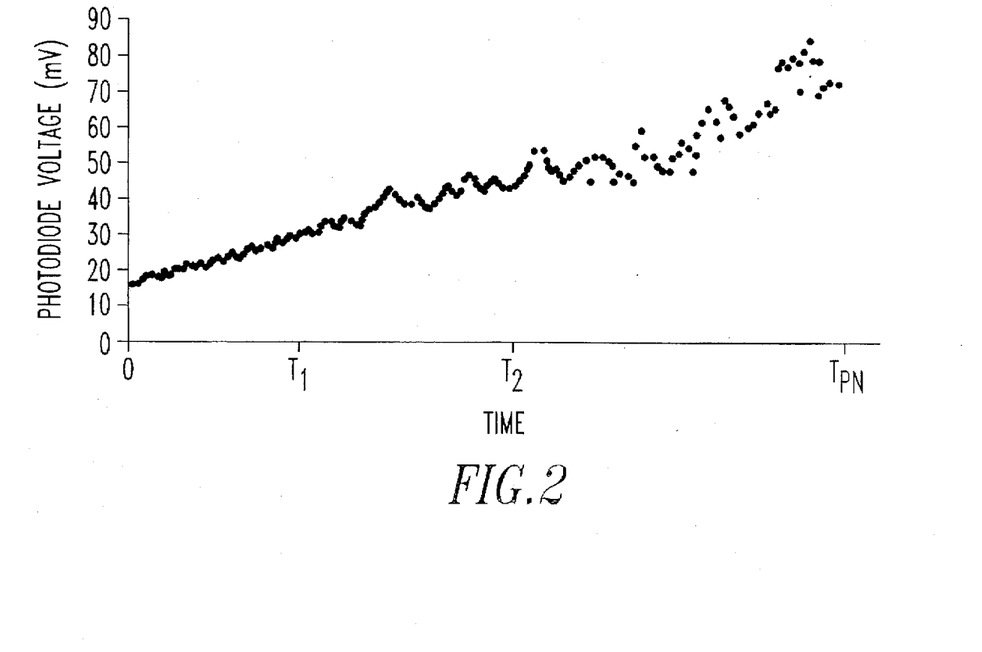
FIG. 2 is an illustration of the development of a negative target substance reaction.
Figure 3:
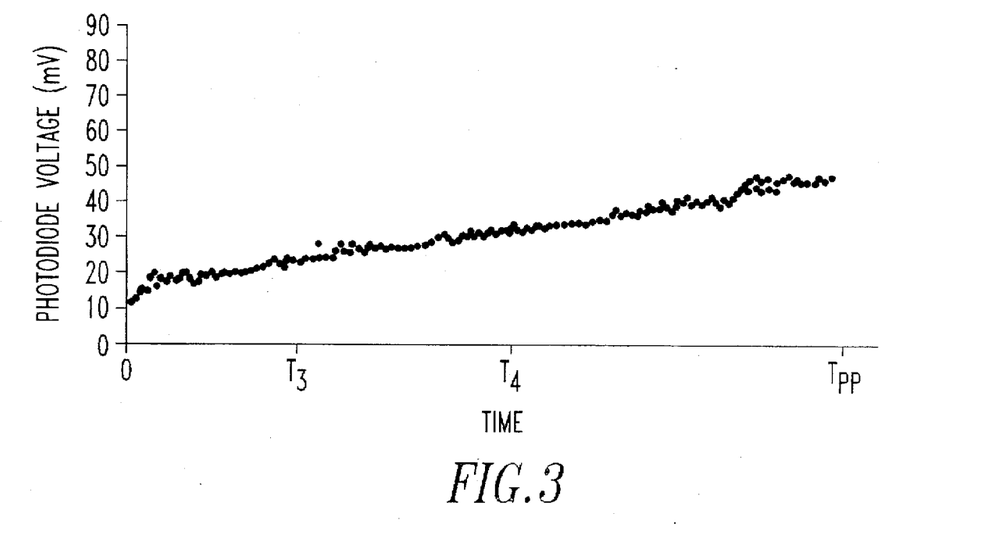
FIG. 3 is an illustration of the development of a positive target substance reaction.

The nature of the optical characteristics may be better understood by reference to FIGS. 2 and 3 showing a negative result and a positive result, respectively, for a single element of the photosensor. In FIG. 2, at times zero through T1, the light transmissivity through the measurand, as indicated by photodiode voltage of a single element, is seen to be relatively low, i.e., less than 30 millivolts. Also, although the portion of light transmitted gradually increases from zero time to time T1, the intensity variation remains small.

The gradual increase in the transmitted portion, seen in FIG. 2, is primarily due to testing near the threshold sensitivity for the given reagent card. In this case, minute aggregations of latex clumps can occur and, while the size of the clumps and the associated clearing of the measurand may be insufficient to produce a negative result, the residual aggregation and clearing may be manifest as the gradually, and slightly, increasing light transmissivity and variation. On the other hand, where larger amounts of the target substance are present, the minute aggregations may not be as prominent and the light transmissivity may remain essentially unchanged over time, resulting in a flatter plot.

Continuing in FIG. 2, between time T1 and time T2 the light transmissivity continues to increase as the negative target substance reaction develops. In addition, an increase in the transmitted light intensity variation is evidenced as the latex clumps begin to form. After time T2, the transmitted portion of light continues to increase, as does the variation in the light intensity. As an analysis progresses, light transmissivity and light intensity variation may each exceed a respective first predetermined threshold such that the negative reaction is detected. In general, a negative reaction tends to remain clumped beyond the expiration of test period $T_{PN}$.

In FIG. 3, a positive target substance reaction can be seen for a single photosensor element. Similar to FIG. 2, the light transmissivity between time zero and time T3 is generally low, and the intensity variation of the transmitted light is small. However, because the latex particles are inhibited from clumping together in the presence of the target substance above the sensitivity threshold, the latex particles remain very fine, leading to a uniformly milky consistency in the measurand and producing little variation in light intensity over time. After time T4, the variation in light intensity remains small compared to light intensity variation in a negative target substance reaction, as seen in FIG. 2.

Given the disparities in the portion of light transmitted and the intensity variation of the light transmitted between the negative target substance reaction and the positive target substance reaction, it is possible to detect a negative reaction when the transmitted portion of light exceeds a first preselected threshold, or the transmitted light intensity variation exceeds a first preselected intensity variation threshold, or both. Once the negative reaction is detected, further analysis may not be necessary, and the substance card may be removed, thus permitting the detector device to be rapidly reused for additional target substance testing.

In the case of FIG. 2, it may be possible to detect a negative reaction in the time between T1 and T2. However, in order to verify a positive result, the analyses in FIG. 3 would continue beyond time T2 until the expiration of the preselected testing period $T_{PP}$. Because the positive result persisted throughout the entire testing period, the result can be reported as a positive result with a substantial degree of confidence. Due to the nature of the latex agglutination test, tests for additional target substances can be accommodated by either adjusting the length of each selectable analysis period or adjusting the selectable number of analysis repetitions, or both. In general, a positive reaction will remain positive for the entire testing period, e.g., 5 minutes, even if a negative result for that particular target substance can be obtained in a very short time, e.g., 10 seconds.

In this way, the method employed herein can be used to detect each of the substances for which a corresponding target substance card is available without the detector device needing to be modified to determine the kind of card or type of target substance for which the test is being performed.

Figure 4:
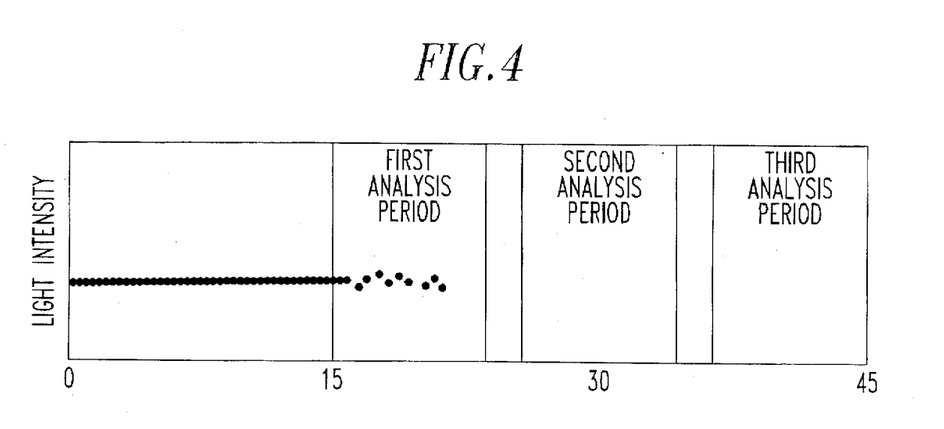
FIG. 4 is an illustration of the development of a negative target substance reaction employing the multiple analysis method according to one embodiment of the invention herein.

FIG. 4 illustrates a negative reaction using the multiple selectable repetition, selectable analysis period substance detection method for a three-analysis-period analysis. In this example, sufficient particle clumping has occurred to permit detection leading to termination of testing during first analysis period.

Figure 5:
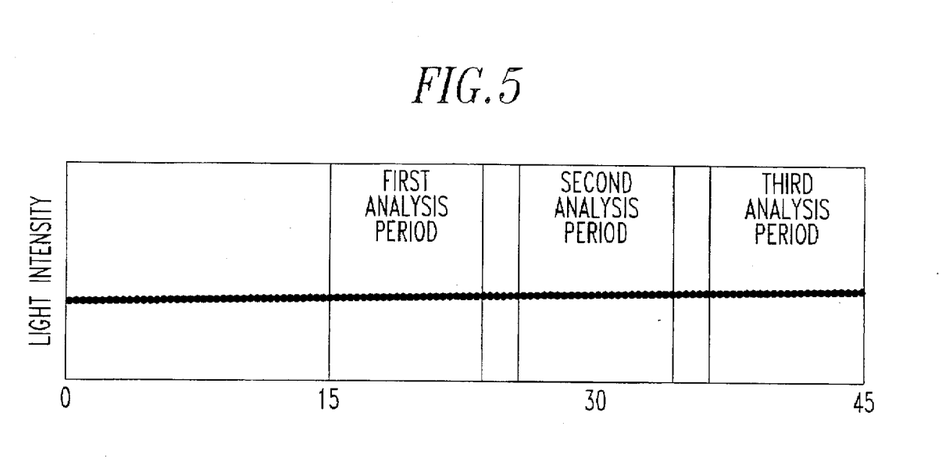
FIG. 5 is an illustration of the development of a positive target substance reaction employing the multiple analysis method according to one embodiment of the invention herein.

FIG. 5 illustrates a positive reaction during a three-analysis-period analysis. Here, low intensity variation can be seen and the measurand is subjected to all three analysis periods. Because the target substance reaction is a positive reaction, the measurand remains milky and translucent during all three periods.

While specific embodiments of practicing the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting to the scope of the invention which is to be given the full breadth of the following claims, and any and all embodiments thereof.

I claim:

1. A method for detecting a plurality of target substances, comprising the steps of:
    (a) collecting a substance sample;
    (b) introducing said substance sample into a substance card having at least one preselected reagent responsive to the presence of each of said plurality of target substances in said substance sample, said substance card having a light-transmissive chamber;
    (c) inserting said substance card into a substance detector device having a photosensor and adapted to receive said substance card;
    (d) mixing said substance sample with said at least one preselected reagent for a preselected mixing period, said mixing producing a measurand having a target substance reaction, said target substance reaction occurring at different rates for different ones of said target substances;
    (e) streaming said measurand through said light-transmissive chamber;
    (f) illuminating said measurand with a predetermined quantity of light for a selectable analysis period and measuring an optical characteristic of said measurand with said photosensor, said optical characteristic corresponding to said target substance reaction;
    (g) selecting said target substance reaction as one of a positive reaction and a negative reaction responsive to said optical characteristic, said positive reaction indicating the presence of one of said plurality of target substances in an amount greater that a first preselected sensitivity amount, and said negative reaction indicating the presence of one of said plurality of target substances in an amount less than said preselected sensitivity amount;
    (h) signaling said negative reaction if said target substance reaction is said negative reaction;
    (i) if said target substance reaction is said positive reaction, repeating steps (e) through (h) for a selectable number of repetitions, said selectable analysis period corresponding to a respective one of said repetitions; and
    (j) signaling said positive reaction if one of said target substance reactions remains said positive reaction after exhausting said selectable number of repetitions.

2. The method of claim 1 wherein said optical characteristic includes at least one of a light transmissivity and a light intensity variation, wherein said positive reaction includes said at least one of light transmissivity being greater than a first predetermined transmissivity threshold and said light intensity variation being less than a first predetermined intensity variation threshold, and said negative reaction includes at least one of said light transmissivity being less than a second predetermined transmissivity threshold and said intensity variation being greater than a second predetermined intensity variation threshold.

3. The method of claim 2 wherein said first transmissivity threshold is greater than said second transmissivity threshold and said second intensity variation threshold is greater than said first intensity variation threshold.

4. The method of claim 1 wherein said target substance reaction is a latex agglutination reaction.

5. The method of claim 1 wherein said selecting further includes monitoring said target substance reaction for an invalidating condition, selecting said target substance reaction as an invalid reaction upon the occurrence of said invalidating condition, and signalling said invalid reaction.

6. The method of claim 5 wherein said invalidating condition includes at least one of missing substance card, defective substance card, misaligned substance card, impaired substance detector device, large bubble formation within said light-transmissive chamber, and streaking of said target substance reaction in light-transmissive chamber.

7. The method of claim 1 wherein a class of detectable target substances includes drugs, explosives, and residues thereof.

8. The method of claim 1 wherein said selectable number of repetitions is three and having a first selectable analysis period, a second selectable analysis period, and a third selectable analysis period, said first selectable analysis period following said preselected mixing period.

9. The method of claim 8 wherein said preselected mixing period is about ten seconds, said first selectable analysis period is about ten seconds, said second selectable analysis period is about fifteen seconds, and said third selectable analysis period is about ten seconds.

10. The method of claim 1 further comprising the step of, after step c, measuring an empty value by illuminating said light-transmissive chamber with a predetermined amount of light and detecting with said photosensor a portion of said predetermined amount of light corresponding to said light-transmissive chamber being generally empty.

* * * * *